US005736389A

United States Patent [19]

Vogelstein et al.

[11] Patent Number: 5,736,389
[45] Date of Patent: Apr. 7, 1998

[54] EB1 NUCLEIC ACIDS

[75] Inventors: Bert Vogelstein, Baltimore; Kenneth W. Kinzler, BelAir, both of Md.

[73] Assignee: The Johns Hopkins University, Baltimore, Md.

[21] Appl. No.: 446,919

[22] Filed: May 22, 1995

[51] Int. Cl.$^6$ ............................ C12N 15/11; C12N 15/12; C12N 15/63
[52] U.S. Cl. ................. 435/320.1; 536/23.1; 536/23.5; 536/24.31; 536/24.3
[58] Field of Search ............................. 536/23.5, 23.1, 536/24.31, 24.3; 435/320.1

[56] References Cited

FOREIGN PATENT DOCUMENTS

WO A 94
21814   9/1994   WIPO.

OTHER PUBLICATIONS

Khan et al, Nature Genetics 2:180, 1992.
Berry et al., Nature Genetics 10:415, 1995.
Okubo et al., Nature Genetics 2:173, 1992.
Fukushima et al, Genomics 122:127 1994.
Database Search Results Accession Nos. R13836 Apr. 12, 1995, Q59948 Mar. 16, 1994, X53520 Jun. 27, 1990, S50474 Dec. 1994.
"Screening Recombinant Libraries" Ch. 6, pp. 6.0.3–6.3.5 in Current Protocols in Mol. Biol, 1990.
EMBL Database, Accession No. T03463 Sequence reference HST03463 from human cDNA clone IB327; 24 Aug. 1993 (created).
EMBL Database, Accession No. D12076 Sequence reference HS000S163 from human HepG2 clone S163; 18 Nov. 1992 (created).
Su et al., "APC Binds to the Novel Protein EB1", Cancer Research 55:2972–2977 (1995).
Database Swissport, Accession No. S50474 Sequence reference S50428 of S. cerevisiae cosmid 9537 Dec. 1994.
Sequence djb/D12076, National Center for Biotechnology Information (NCBI), Blast Network Jan. 1995.
Sequence gb/T03463, National Center for Biotechnology Information (NCBI), Blast Network Jan. 1995.
Sequence dbj/D12080, National Center for Biotechnology (NCBI), Blast Network Jan. 1995.
Sequence emb/Z13306, National Center for Biotechnology Information (NCBI), Blast Network Jan. 1995.
Sequence gb/T23427, National Center for Biotechnology Information (MCBI), Blast Network Jan. 1995.
Sequence gb/T31547, National Center for Biotechnology Information (NCBI), Blast Network Jan. 1995.
Sequence gb/T30188, National Center for Biotechnology Information (NCBI), Blast Network Jan. 1995.
Sequence emb/Z21248, National Center for Biotechnology Information (NCBI), Blast Network Jan. 1995.
Sequence emb/Z38235, National Center for Biotechnology Information (NCBI), Blast Network Jan. 1995.
Sequence gb/T10870, National Center for Biotechnology Information (NCBI), Blast Network Jan. 1995.
Sequence emb/Z21247, National Center for Biotechnology Information (NCBI), Blast Network Jan. 1995.
Sequence gb/L36092, National Center for Biotechnology Information (NCBI), Blast Network Jan. 1995.
Sequence emb/Z46175, National Center for Biotechnology Information (NCBI), Blast Network Jan. 1995.
Sequence emb/Z19434, National Center for Biotechnology Information (NCBI), Blast Network Jan. 1995.
Sequence gb/M85402, National Center for Biotechnology Information (NCBI), Blast Network Jan. 1995.
Sequence emb/Z15792, National Center for Biotechnology Information (NCBI), Blast Network Jan. 1995.
Sequence gb/T11200, National Center for Biotechnology Information (NCBI), Blast Network Jan. 1995.
Sequence gb/I03335, National Center for Biotechnology Information (NCBI), Blast Network Jan. 1995.
Sequence gb/M74555, National Center for Biotechnology Information (NCBI), Blast Network Jan. 1995.
Sequence dbj/D34782, National Center for Biotechnology Information (NCBI), Blast Network Jan. 1995.
Sequence dbj/D37609, National Center for Biotechnology Information (NCBI), Blast Network Jan. 1995.
Sequence fb/U12386, National Center for Biotechnology Information (NCBI), Blast Network Jan. 1995.

Primary Examiner—Lila Feisee
Assistant Examiner—Nancy A. Johnson
Attorney, Agent, or Firm—Banner & Witcoff, Ltd.

[57] ABSTRACT

Inactivation of the APC minor suppressor gene plays an important role in the development of both sporadic and familial forms of colorectal cancers. The majority of these mutations result in the loss of the carboxyl terminus of the APC protein. A cellular protein, EB1, that associates with the carboxyl terminus of APC both in vitro and in vivo has been identified. The EB1 gene is predicted to encode a 268 amino acid protein without significant homology to any protein with known function.

6 Claims, 11 Drawing Sheets

FIG. 1A

```
  1                                                                                      ▲
  1    A   CGA GAC GAA GAC GGA ACC GGA GCC GGT TGC GGG CAG TGG
                                        ▲
  7    Ser Thr Ser Val Thr Ser Asp Asn Leu Ser Arg His Asp Met
 83    TCA ACG TCA GTG ACC AGT GAT AAC CTA AGT CGA CAT GAC ATG

35    Ile Glu Gln Leu Cys Ser Gly Ala Ala Tyr Cys Gln Phe Met
167    ATC GAA CAG TTG TGC TCA GGG GCT GCG TAT TGT CAG TTT ATG
                                    ▲
 63    Phe Gln Ala Lys Leu Glu His Glu Tyr Ile Gln Asn Phe Lys
251    TTC CAA GCT AAG CTA GAA CAC GAG TAC ATC CAG AAC TTC AAA
                                                ▲
 91    Ile Pro Val Asp Lys Leu Val Lys Gly Lys Phe Gln Asp Asn
335    ATT CCT GTG GAC AAA TTA GTA AAA GGA AAG TTT CAG GAC AAT

119    Tyr Asp Gly Lys Asp Tyr Asp Pro Val Ala Ala Arg Gln Gly
419    TAT GAT GGA AAA GAC TAT GAC CCT GTG GCT GCC AGA CAA GGT
                                            ▲
147    Asn Lys Pro Lys Lys Pro Leu Thr Ser Ser Ser Ala Ala Pro
503    AAT AAA CCG AAG AAG CCT CTC ACT TCT AGC AGT GCA GCT CCC

175    Ala Gly Pro Gly Val Val Arg Lys Asn Pro Gly Val Gly Asn
587    GCT GGC CCT GGT GTG GTG CGA AAG AAC CCT GGT GTG GGC AAC

203    Leu Lys Leu Thr Val Glu Asp Leu Glu Lys Glu Arg Asp Phe
671    TTG AAA CTT ACT GTT GAA GAC TTG GAG AAA GAG AGG GAT TTC
```

FIG. 1B

```
                                  Met Ala Val Asn Val Tyr      6
ACG CGG TTC TGC CGA GAG CCG AAG ATG GCA GTG AAC GTA TAC        82

Leu Ala Trp Ile Asn Glu Ser Leu Gln Leu Asn Leu Thr Lys       34
CTG GCC TGG ATC AAT GAG TCT CTG CAG TTG AAT CTG ACA AAG       166

Asp Met Leu Phe Pro Gly Ser Ile Ala Leu Lys Lys Val Lys       62
GAC ATG CTG TTC CCT GGC TCC ATT GCC TTG AAG AAA GTG AAA       250

Ile Leu Gln Ala Gly Phe Lys Arg Met Gly Val Asp Lys Ile       90
ATA CTA CAA GCA GGT TTT AAG AGA ATG GGT GTT GAC AAA ATA       334

Phe Glu Phe Val Gln Trp Phe Lys Lys Phe Phe Asp Ala Asn      118
TTT GAA TTC GTT CAG TGG TTC AAG AAG TTT TTC GAT GCA AAC      418

Gln Glu Thr Ala Val Ala Pro Ser Leu Val Ala Pro Ala Leu      146
CAA GAA ACT GCA GTG GCT CCT TCC CTT GTT GCT CCA GCT CTG      502

Gln Arg Pro Ile Ser Thr Gln Arg Thr Ala Ala Ala Pro Lys      174
CAG AGG CCC ATC TCA ACA CAG AGA ACC GCT GCG GCT CCT AAG      586

Gly Asp Asp Glu Ala Ala Glu Leu Met Gln Gln Val Asn Val      202
GGA GAC GAC GAG GCA GCT GAG TTG ATG CAG CAG GTC AAC GTA      670

Tyr Phe Gly Lys Leu Arg Asn Ile Glu Leu Ile Cys Gln Glu      230
TAC TTC GGA AAG CTA CGG AAC ATT GAA TTG ATT TGC CAG GAG      754
```

FIG. 1C

|  | Asn | Glu | Gly | Glu | Asn | Asp | Pro | Val | Leu | Gln | Arg | Ile | Val | Asp |
|---|---|---|---|---|---|---|---|---|---|---|---|---|---|---|
| 231 | AAC | GAG | GGG | GAA | AAC | GAC | CCT | GTA | TTG | CAG | AGG | ATT | GTA | GAC |
| 755 |
| 259 | GGG | GGC | CCA | CAG | GAG | TAC | GTT | GAA | TAT | TAA | CAG | CCT | GGA |
| 839 | TTA | ACT | GTA | AAA | GAC | TCC | TCA | TTG | TTA | TCC | TTA | GAG | GAC | TCA |
| 923 | CAC | TTT | GCA | CCT | GAG | GTT | CTT | TTC | CAA | CAA | TAA | GTT | TGA | GTT |
| 1007 | GGT | TCA | TCA | GAG | TCA | AGA | GGC | TGA | CCG | TGG | GGC | TCA | CCA |
| 1091 | TAT | GCT | GAG | GTG | AAA | CAG | GCG | GAG | AAA | AAA | TGT | AAA | GAC | TGA |
| 1175 | AGT | AAA | TGC | CTT | GCG | ACC | TCA | GTG | TAA | ATG | CTT | CCA | CAT | TTC |
| 1259 | TTG | TGT | CTG | GGA | AGG | AGT | ATT | TAA | AAT | ACC | TTG | GAA | CCT | TTG | GAA |
| 1343 | GGC | CTA | GGC | TTT | GGT | CTA | GGC | CAG | GGA | TTT | AAA | TTG | CCC |
| 1427 | AAA | AGC | AAG | AGG | CAT | TGC | CTG | ACA | AAT | AGA | GGA | TGT | GTT |
| 1511 | GCA | TTT | CTC | TAT | TTT | TCC | CGT | GAT | CCC | GAA | ATT | TCT | ATG | TAT |
| 1595 | CAA | CTA | CTT | TTC | GGG | ACT | TGC | AGT | TAT | CCC | CAT | CTC | TTG | AAT |
| 1679 | CCA | CGT | TCT | TCT | TGC | CTG | TGC | CCA | CCC | TTG | CCC | TTC | ACT | CCT |
| 1763 | CAG | GCA | GAT | CAT | CTG | GCT | CTC | AGT | GCA | AGT | TCT | GGG | ACT | GGC |
| 1847 | CCA | GGC | TGG | GGT | GTT | TTC | GGT | ATC | TGC | TGG | ACC | CAG | CTC | TCC |
| 1931 | GAT | AAA | ATT | CAT | TAG | TGT | GTT | ACT | CTC | TCA | TAA | TTT | TCT | TTT |
| 2015 | AAA | ATA | CTT | CAT | CAT | TCC | TTA | ACT | CTC | CCT | CAT | TTG | CTT | TGC | CCA |
| 2099 | TGT | CTC | ACC | CAC | CAC | TAC | TGA | GAT | TCA | AAA | GCC | CCT | TGT | GTA | TTT |
| 2183 | TAG | AAA | ATG | AGT | ATT | TTA | TGA | TTA | AAC | TAG | TGT | CCA | TTC | CAT |
| 2267 | ACA | CCA | AAA | AAT | GCA | AGT | AGT | TAA | AAC | TGT | TGT | TTG | TGA | TGA |
| 2351 | GCC | CTA | ATG | TTC | CAT | TTT | ATT | GGG | AAC | CCA | TTT | CCT | TTC | ACC | TGG |
| 2519 | ATA | AAA | TTC | TGT | ATT | TCA | AAA | A |

FIG. 1D

| | | | | | | | | | | | | | | |
|---|---|---|---|---|---|---|---|---|---|---|---|---|---|---|
| Ile | Leu | Tyr | Ala | Thr | Asp | Glu | Gly | Phe | Val | Ile | Pro | Asp | Glu | 258 |
| ATT | CTG | TAT | GCC | ACA | GAT | GAA | GGC | TTT | GTG | ATA | CCT | GAT | GAA | 838 |

```
CCA GCA GAG CAA CAT CGG AAT TCT TCA CTC CAA ATC ATG TGC   268 922
CTG GTT TCT TTT CAT AAG CAA GTA CCT CTT AAA GTG          1006
AGG AGC TTT TAC CTT GTA CAC GCA CAG TAT CAT CTA GTT      1090
TGC GGA TGC GGG TCA CAC TGA ATG CTG GAG CAT ATG TAA      1174
ATT GAA TTT TAA GCT AAT GTG AAA TCA GAG AGA GTT ATG ATA  1258
AAA ATA TAA AAT GTA ACA TGA CAA GAG ATT GTA GTA ACA      1342
CCT GCT GTC AAC AGG TCT TAC AGG GCT TTG CGT TTG ACA      1426
TGT AAA GTT ATT TGG TGT CAT TGA CCA ATT TGA ACC CTC ATA  1510
TCA GCC CTG AGA TGT TAC AGT GCT AGA CCC TCC CAG CTA      1594
TAT TTT TTG GGG AAG TGA TTT CTT GTG AGT TTA CAT TGA      1678
GGG GAT TGT ATC CCA TAC TGC TGT TTA GAG TTA ATC TAA      1762
CTT TGG CTC CTT GAA CAG AGG CCA TGC AGG TTG CAT TTA      1846
AAA GGG AGT GGT CAG TGA CCA TCG TGC TTA GAA GTG CAG      1930
ACT GTA ATC CGA ATA CTT AAT TGC ACT TTG CCT TTT CTG GGA  2014
GCG GAA AAT ACA GTA CCG CTG GAA TAA TCT AAT CTC ATA TTT  2098
CAG CCT ATT CAG TTC CTT TTG GCA TAA TTA TTC ATA ATG      2182
GTA TTG ATT TGT TGG TGG TAG CTT GTC GGA AAA TGC AAA ATG  2266
GCT CTG TGT GGA AGG CAG AAA ACC CTG ATT CAG TGT GTG      2350
CAG TGG TGC TAT CAG GCC TTT GTG GCC TAG ACT TTA TGA TTA  2434
TCT TTC TTG ACA GGG TTT TCT ACT TTA AAC AGT TTC TAA      2518
                                                          2540
```

FIG. 5A

```
EB1    ---------------------------------------------MAVNVMSTSVTSDNLSRHDMLAWINESLQLNLTKTEQLCSGAAYCQ    46
EB2    --------------------------------------------------------IAWMNDIVSLNYTKVEQLCSGAAYQQ              26
Z19434 dedppprsrrpepqplpqrprhlspppppeppralwgMAVNVMSTSVTSENLSRHDMLAWMNDSLHLNYTKTEQLCSGAAYCQ           85
M85402 --------------------------------------------------------------------------------              0

EB1    FMDMLFPGSIALRKKVKFQAKLEHEYIQNFKILQAGFKKRMGVDKLIIPVDKLIVKGKFQDNFEFVQWFKKRFDANYDGKDYDPVAARQ      131
EB2    FMDMLFPGCISLRKKVKFQAKLEHEYIHNFKILQASFKKRMNVDKVIIPVEKLIVKGRFQDNLDFIQWFKKFYDANYDGKEYDPVEARQ      111
Z19434 FMDMLFPGCVHLRKVKFQQKLQHXYIH---------------------------------------------------------           112
M85402 --------------NFKMLQXAFKKMQVDKTIPVEKLIVKGKFQDNFXFIQWFKKXFDANYDGKDYNPLLARQ                        58

EB1    GQETAVAPSLVAPAINKPKKpltssisaapqrpistqrtaaatpkagpgtvvrknpgigvgngddeaaelmqqvnvlkltvedlekerdf   216
EB2    GQDAIPPPPDPGEQIFNIPKKshhanisptagaakfkfqx--------------------------------------                  149
Z19434 --------------------------------------------------------------------------------             112
M85402 GQDVAPPPNPVPQrtsptgpknmqtsgrlsnvappcilrkxppsarngghetcphslhsnqq--                                120

EB1    yfgklrnielicqenegendpvlqrivdilyatdegfvipdeggpqeeqeey                                            268
EB2    ---------------------------------------------------                                             149
Z19434 ---------------------------------------------------                                             112
M85402 ---------------------------------------------------                                             120
```

FIG. 5B

```
EB-1     mavnrvystsvtsdnlSRHDMIAWINESLQLNLTKIEQLCSGAAYCQFMDMLFpGSTALKKVKFQAKLEHEYIQNFKILQAGFKRM      85
Yer016p  msagige-------SRTELITWINGLILNLNYKKIEECGTGAAYCQTMDSIY-GDIPMNRVKFNATAEYEFQTNYKILQSCFSRH        76

EB-1     QVDKLTPVDKLIVKGKFQDNFEFVQWFKKFFDANYDGKDYDPVaarggetavapslvapal----------NKPKKPLTSSSAAPQ    161
Yer016p  GIEKTVYVDKLITRCKFQDNLEFLQWLKKHWIRHKDESVYDPD----------arrkyrpiitrNSATKPRTVSNPTTA          144

EB-1     RPISTQRTAAAPKACPGVVRKNPGVg----------NGDDEAAEIMQQVNVLKLTVEDLEKERDFYFGKLRNIEL              226
Yer016p  KRSSSTQTGSAMSGGIATRHSSLGIngsrktsvtgqglvaiqaeltKSQETIGSINEEIEQYKGTVSTLEIEREFVFNKLRDIEI    229

EB-1     Icqenegenidpv----------LQRIVDIILYATDEGFVIIPDeggpqeeqeey----------                        268
Yer016p  livhttqdlihegvykfndetitghgngnggallrfVKKKVESILYATAEGFEMNDgedelnqdknlgehgtvpnqggyansngevng 314

EB-1     ----------                                                                              268
Yer016p  negsnhdvimqndegevgvsnnliideetf                                                          344
```

EBI NUCLEIC ACIDS

This invention was made with support from the National Institutes of Health, Grant No. CA57345. The U.S. government therefore retains certain rights in the invention.

BACKGROUND OF THE INVENTION

The APC gene (adenomatous polyposis coli) was originally isolated by virtue of its alteration in familial and sporadic forms of colorectal cancer (1–4). Germline mutations of the APC gene account for most cases of familial adenomatous polyposis (FAP), an autosomal, dominantly inherited disease that predisposes patients to multiple colorectal polyps and cancer (reviewed in 5). APC mutations have also been found in cancers of the central nervous system. While FAP patients with germline mutations of APC account for less than 1% of colorectal cancers in the United States, somatic mutations of APC occur in the majority of colorectal adenomas and cancers (6–9). These alterations appear to occur early as they can be identified in the smallest identifiable lesions including dysplastic aberrant crypt foci (6, 10, 11). The vast majority of both germline and somatic APC mutations are predicted to result in truncation of the APC protein due to either nonsense or frame-shifting mutations (5,6,7,8,9). Likewise, mice carrying homologous germline truncating mutations of APC are also predisposed to intestinal tumors (8, 9, 10). Altogether, these results strongly suggest that APC mutations are an early if not initiating event in the development of both sporadic an inherited forms of colorectal cancer.

While disruption of normal APC function clearly plays a role in colorectal tumorigenesis, what this function might be remains unclear. The APC gene is predicted to encode a protein of 2843 amino acids with limited functional homology to known proteins. The primary structure contains several Armadillo repeats that are shared by proteins with apparently diverse functions (3, 15) as well as several regions of heptad repeats of the type that mediate oligomerization via coiled-coil structures (3). Indeed, the amino terminus of APC, which has a very strong potential for forming coiled-coil structures, has been shown to mediate the homo-oligomerization of APC protein (16, 17). Three additional repeats located between amino acids 1000 and 1200 of APC mediate an associate with α and β-catenins, critical cytoplasmic components of cadherin cell adhesion (18, 19). In addition, wild-type but not mutant forms of APC have been shown to associate with microtubule cytoskeleton (20, 21).

While the aforementioned biochemical characteristics of APC provide important clues to its function, other functions remain undefined. Because mutant APC proteins almost uniformly lack their carboxyl terminus, we hypothesized that the carboxyl terminus of APC interacts with proteins that are essential for its normal function. To test this hypothesis we attempted to identify a protein that associates with the carboxyl terminus of APC.

SUMMARY OF THE INVENTION

It is an object of the invention to provide a nucleic acid molecule encoding a protein which binds to APC.

It is an object of the invention to provide a protein molecule which binds to APC.

It is another object of the invention to provide nucleic acid molecules which can be used to detect genes involved in neoplasia in a sample.

It is yet another object of the invention to provide methods for determining a predisposition to colorectal and other neoplasms.

It is still another object of the invention to provide antibodies useful for detecting proteins which bind to APC.

It is an object of the invention to provide methods for assessing susceptibility to colorectal and other cancer.

It is an object of the invention to provide methods for diagnosing cancer.

It is still another object of the invention to provide methods to assess treatment options for a cancer.

It is yet another object of the invention to provide methods to assess the status of APC alleles in a cell.

These and other objects of the invention are provided by one or more of the embodiments described below. In one embodiment of the invention a nucleic acid molecule is provided which Comprises an EB1 DNA according to SEQ ID NO: 1. Also provided is a molecule which may contain at least 12, 18, or 20 contiguous nucleotides of EB1 coding sequence. Also provided is a molecule which encodes at least about 6, 8, 10, or 20 contiguous EB1 amino acids.

In another embodiment of the invention an isolated and purified EB1 protein is provided. The protein has an amino acid sequence according to SEQ ID NO:2. Polypeptides having at least 6, 8, 10, or 20 contiguous amirto acids of said sequence are also provided.

In still another embodiment of the invention a method for determining a predisposition to or a diagnosis of colorectal and other neoplasms is provided. The method comprises the step of: determining one or more mutations in one or more EB1 alleles of a human tissue, wherein wild-type EB1 is as shown in SEQ ID NO:1.

In one embodiment of the invention a method for determining a predisposition to or diagnosis of colorectal and other neoplasms is provided. The method comprises the step of: assaying protein complexes in a cell, wherein said protein complexes comprise APC and EB1, wherein absence of said complexes or reduction in level of said complexes indicates a predisposition to neoplasms.

In another embodiment of the invention an antibody preparation is provided. The antibody is specifically immunoreactive with an EB1 protein according to SEQ ID NO:2.

According to still another aspect of the invention a method for determining a diagnosis or predisposition to cancer is provided. The method comprises the step of: testing a human tissue to determine if the tissue expresses less EB1 gene product than a normal human tissue or no EB1 gene product.

In another embodiment of the invention a method is provided to assess treatment options for a cancer. The method comprises the step of: contacting a lysate of cancer cells with EB1 protein and detecting the formation of protein complexes comprising said EB1 protein, a lysate which fails to form complexes indicating cancer cells which are good candidates for treatment with cyclooxygenase inhibitors.

In yet another embodiment of the invention, a method is provided to assess the status of APC alleles in a cell. The method comprises the step of contacting a lysate of cells with EB1 protein, a lysate which fails to form complexes indicating cancer cells which may lack wild-type APC.

These and other embodiments of the invention provide the art with the identity of a gene and a protein which are involved in the suppression of neoplasia.

BRIEF DESCRIPTION OF THE DRAWINGS

FIG. 1 shows the nucleotide and predicted amino acid sequences of EB1. The arrowheads above the sequences indicate the 5' termini of different EB1 cDNA clones isolated by yeast two hybrid screening. The predicted amino acid sequence begins at nucleotide 65 and ends at the nucleotide 868. The nucleotide sequence has been deposited with Genbank (#U24166).

FIG. 2 shows in vitro Binding of EB1 to APC.

FIG. 5 shows human and yeast EB1 homologues. FIG. 5A shows an amino acid sequence comparison among human EB1 homologues. EB2 represents the amino acid sequence predicted from the nucleotide sequence of a contig of 3 different EST's (Z46175, T17004 and Z42534.) The Z19434 and M85402 lines show the predicted amino acid sequences of these two EST's, respectively. Because of the lack of overlap between Z19434 and M85402, we could not determine whether they represented one or two genes. "_" indicates that no sequence information was available at that position. FIG. 5B shows an amino acid sequence comparison between human EB1 and a potential yeast EB1 homolog. The sequence of Yeo16p is predicted from an open reading frame (ORF) from yeast chromosome V as described in the text. "-" indicates gap introduced to allow the best alignment between the two sequences. In both FIGS. 5A & 5B, blocks of homology are capitalized and shaded according to their mean scores.

DETAILED DESCRIPTION OF THE PREFERRED EMBODIMENTS

Figure 2A:
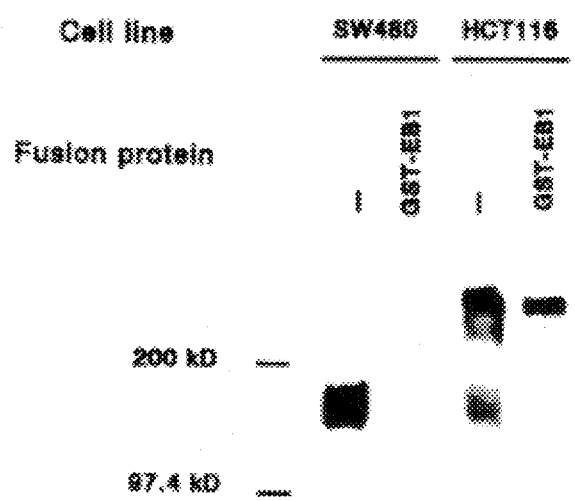
FIG. 2A shows binding of cellular APC to GST-EB1 (glutathione S-transferase=GST) fusion protein. SW480 and HCT116 are human colorectal cancer cell lines that express truncated and full length APC, respectively (19). Protein from total cell lysates (−) or protein bound by GST-EB1 fusion protein (GST-EB1) were analyzed by Western blot analysis with APC-specific monoclonal antibody FE9 (19).

We have identified a eDNA that codes for a protein that interacts with the carboxyl terminus of APC. This interaction was clearly demonstrated by binding of cellular APC to recombinant EB1 and by binding of cellular EB1 to recombinant APC. The association between EB1 and APC in mammalian cells was also demonstrated in cells cotransfected with vectors expressing these two proteins. Because almost all previously identified APC mutations result in the truncation of the APC protein, these mutant APC proteins cannot associate with EB1. This observation strongly suggests that the interaction between APC and EB1 is important for the normal function of APC and that loss of this association is essential for the development of colorectal cancer. Mutation of EB1 is one way that a cell can lose this association.

EB1 nucleic acid molecules according to the present invention include both ribonucleic acids and deoxyribonucleic acids. They may be incorporated as a part of a vector, such as a virus, phage, plasmid, minichromosome, etc. A vector typically contains an origin of replication which allows for independent replication of the nucleic acids of the vector and any insert it may be carrying. Suitable vectors may be chosen for a particular purpose, as is well within the skill of the art. Isolation and purification of nucleic acid molecules from other nucleic acid molecules and from other cellular components can be accomplished as is well known in the art. Nucleic acid molecules comprising at least about 12, 18, or 20 nucleotides of EB1 coding sequence can be used inter alia as probes and primers. Probes are typically labelled with a detectable label such as a radionuclide, an enzyme, or ligand. Primers may have restriction enzyme sites or promoters appended, as may be desirable for cloning or in vitro protein synthesis. Nucleic acid molecules encoding at least about 6 or 20 contiguous amino acids of EB1 can be used for expressing fragments of EB1, for example for use in fusion proteins or as antigens or immunogens. The nucleotide sequence of wild-type EB1 is provided in SEQ ID NO: 1. The amino acid sequence of EB1 protein is provided in SEQ ID NO:2.

EB1 protein may be isolated and purified from human cells, from transformed mammalian, other eukaryotie, or prokaryotic cells. Purification may be accomplished employing antibodies which are specific for EB1, such as AE9, EA3, and GD10, as provided herein. Other antibodies can be used which are made using all or a portion of EB 1 as an immunogen. Affinity methods may also be used which take advantage of the binding of EB1 to APC. EB1 may also be synthesized chemically or in an in vitro system, as described in more detail below. Portions of EB1 which contain at least 6 or 20 contiguous amino acids according to SEQ ID NO:2 can be used in assays and as immunogens. These can be synthesized and isolated according to established techniques with the benefit of the sequence information provided herein.

Predisposition to colorectal and other neoplasms can be determined by examination of a sample for a mutation in an EB1 gene. Such other cancers include, but are not limited to desmold tumors, osteomas, glioblastomas, medulloblastomas and other tumors of the central nervous system. Examination can be done by comparison with the wild-type sequence provided in SEQ ID NO: 1 or to the EB1 found in human tissues which are normal. It can also be done by determining diminished expression of EB1 protein or message, or failure of EB1 to form complexes with APC. Methods for determining mutations include PCR, sequencing, restriction mapping, S1 nutlease mapping, and hybridization with allele-specific probes. Any method known in the art can be used. Methods for determining diminished EB1 expression or failure to form complexes with APC can be determined using techniques such as immunoprecipitation, immunoblotting, immunohistochemistry, etc. Antibodies which are particularly useful for such purposes are monoclonal antibodies AE9, EA3 and GD10, whose isolation and production are discussed in more detail below. Polyclonal antibodies can also be used, especially if purified to render a preparation monospecific. Samples which may be tested for assessing susceptibility to colorectal cancer include blood, chorionic villi, fetal trophoblasts, amniotic fluid, and blastomeres of pre-implantation embryos. Solid tissues can also be tested to determine predisposition and/or diagnosis.

Assays using EB1 can be used to assess the status of APC alleles, since according to the present invention EB 1 and APC interact. Thus, for example, a lysate of cells can be contacted with EB1 protein and the formation of protein complexes comprising EB1 protein can be detected. If the lysate fails to form complexes with EB 1 the cells are likely cancer cells which lack wild-type APC. Other means for measuring the interaction of EB1 with APC can be used to provide such information.

The drug sulindac has been shown to inhibit the growth of benign colon tumors in patients with familial adenomatous polyposis (FAP), presumably by virtue of its activity as a cyclooxygenase inhibitor (Waddell et at., J. Surg. Oncology 24(1), 83 (1983); Wadell, et at., Am. J. Surg., 157(1), 175 (1989); Charneau et at., Gastroenterologie Clinique at Biologique 14(2), 153 (1990)). Cyclooxygenase is required to convert arachidonic acid to prostaglandins and other biologically active molecules. Since FAP is attributed to mutations in APC, treatment options for a cancer may be assessed using EB1. EB1 can be used as described above to assess the status of APC alleles. Cells which fail to form protein complexes with EB1 are likely cancer cells which are good candidates for treatment with cyclooxygenase inhibitors, such as sulindac.

EXAMPLES

Example 1

This example describes the isolation of a gene which encodes a protein which interacts with the carboxy terminus of APC.

We used a modified yeast two hybrid system (22,23) to screen a HeLa cDNA library for proteins interacting with the carboxyl terminus (codons 2167 to 2843) of APC. A total of 90 positive clones with the appropriate phenotype were identified after screening one million transformants. The cDNAs isolated from 67 out of these 90 clones were able to confer the correct phenotype when retransformed into the test strain of yeast. The nucleotide sequences of both ends of each cDNA were determined and were compared to each other. Forty-eight of these cDNAs were found to be derived from a same gene and could be separated into 11 groups according to their length (FIG. 1 ). We chose to characterize this cDNA in detail and named it EB1 (for EcoRI fragment binding protein 1). The fusion proteins encoded by two independent eDNA clones did not interact with amino proximal residues 6 to 1013 when tested in the two hybrid assay.

Northern blot analysis with probes to EB1 identified a single 2.4 kb transcript. Because the largest EB1 cDNA isolated by interaction trap method was 1.4 kb, we screened a human fetal brain eDNA library to isolate the full length cDNA. None of the newly isolated eDNA clones had additional 5' nucleotide sequence but many of them had additional 3' nucleotide sequence extending the length of the cloned message to 2.4 kb. Furthermore, no additional 5' sequence was obtained after screening three 5'-RACE cDNA libraries. Together, these results suggest that the full-length message for EB1 had been isolated. Nucleotide sequence analysis of the overlapping eDNA clones revealed an ORF extending from nucleotide 1 to 868 (FIG. 1). If translation initiated at the first methionine, EB1 would be predicted to encode a 268 amino acid protein with a predicted molecular weight of 30 kD.

Methods: Two hybrid screening. The modified yeast two hybrid system, the cDNA library and screening the eDNA library using this system have been described (22, 23). The bait was made by inserting a 2.5 Kb EcoRI fragment of APC containing nucleotides nucleotide 6498 to 8950 into the Sinai site of LexA(1–202)+PL(24) after making the EcoRI fragment blunt-ended using the Klenow fragment of DNA polymerase I.

EXAMPLE 2

This example demonstrates the in vitro and in vivo binding of APC to EB1.

To confirm and extend the two hybrid results, we tested the direct interaction between EB1 and APC using an in vitro binding assay. The carboxyl terminal 163 residues of EB1 were expressed as a glutathione-S-transferase fusion protein in E. coli. This fragment was expected to bind APC because it included more of EB1 than several of the EB1 eDNA clones originally isolated by the yeast interaction trap method. As expected, this fusion protein was able to associate with the full-length APC from cell lysates, but was unable to bind to mutant APC that lacked the putative EB1 binding region (FIG. 2A). This result clearly showed that EB 1 interacts with endogenous APC and that this interaction requires the carboxyl terminus of APC.

Figure 2B:
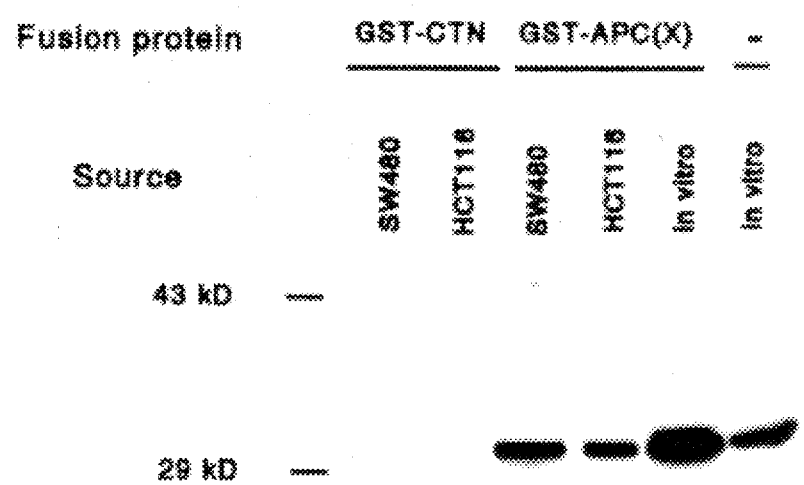
FIG. 2B shows the binding of EB1 to GST-APC fusion protein. GST-CTN has been described (19) and was used as a negative control. SW480 and HCT116 cells were metabolically labelled with $^{35}$-Met and incubated with the GST fusion proteins as indicated. In vitro transcribed and translated EB1 (in vitro) was run on gel directly (−) or following binding to GST-APC(X) fusion protein as indicated. Proteins were detected by fluorography.
Figure 2C:
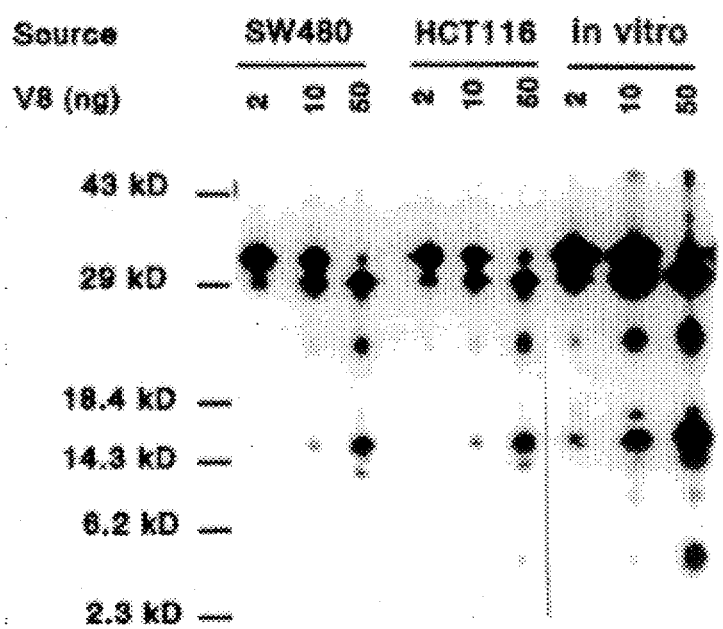
FIG. 2C shows one dimensional peptide mapping. Cellular (SW480, HCT116) and in vitro translated (in vitro) EB1 proteins were isolated by binding to GST-APC(X) and subjected to one dimensional peptide mapping as described (19).

To test whether APC could bind endogenous EB1, we expressed amino acid codons 2167 to 2843 of APC as a GST fusion protein (GST-APCE) and incubated the purified fusion protein bound on the ghtathione agarose with lysates prepared from metabolically labeled colon cancer cell lines. The APC fusion protein bound a 30 kD cellular protein bound which had identical mobility to the EB1 expressed in vitro (FIG. 2B). To confirm that this 30 kD protein was indeed EB1, we compared the one-dimensional peptide map of this 30 kD protein with that of EB1 expressed in vitro. The peptide maps of these proteins were identical (FIG. 2C). This result also provided additional evidence that the first codon for methionine in the EB1 eDNA is the translational initiation codon.

Methods: GST fusion proteins. The pGSTagEB1A expression vector was constructed using an EcoRI fragment (nucleotides 317 to 899 of EB1) of an EB1 cDNA clone isolated by interaction trap screening. After subcloning into the EcoRI site of pBluescript SK II, the EcoR1 fragment was excised as a BamHI-SalI fragment and inserted into the BamHI and XhoI sites of pGSTag (25). The pGSTagEB1B expression vector constructed by inserting a 1.8 Kb SalI-HindIII fragment (nucleotides 40 to 2091) of an EB1 eDNA clone isolated from human fetal brain eDNA library into the SalI and HindIII sites of pGSTag. The pGSTagAPCE expression vector was constructed by inserting the 2.5 Kb EcoKI fragment of APC eDNA, identical to that used for making the bait for two hybrid screening, into the EcoRI site of pGSTag. The expression and purification of fusion proteins were carried out as described (19).

Methods: PCR and in vitro expression of EB1. The EB1 coding region was amplified by using the upstream primer 5'-GGATCCTAATACGACTCACTATAGGGAGACCAC-CATGGCAGTGAACG TATACTC-3' and the downstream primer 5'-ATTTCTCCACTGAGGTCGC3'. The upstream primer contains the sequence of the promoter for the T7 DNA polymerase and the first 20 nucleotides of the EB1 coding sequence. The downstream primer locates at the 3' untranslated region of EB1. The PCR reaction was carried out using an isolated cDNA clone as the template with 35 cycles of 30 sec at 95° C., 1 min at 50° C., and 1 min at 70° C. The PCR product was using directly in a coupled in vitro transcription and translation reaction as described (26).

Methods: in vitro binding assay. Metabolically labelled protein extracts from the human colorectal cancer cell lines SW480 and HCT116 were used for the in vitro binding assay. Metabolic labeling, preparation of cell lysates, in vitro binding, and peptide mapping were carried out as described (19).

Example 3

This example demonstrates the in vivo association of EB1 and APC by co-immunoprecipitation.

Figure 3:
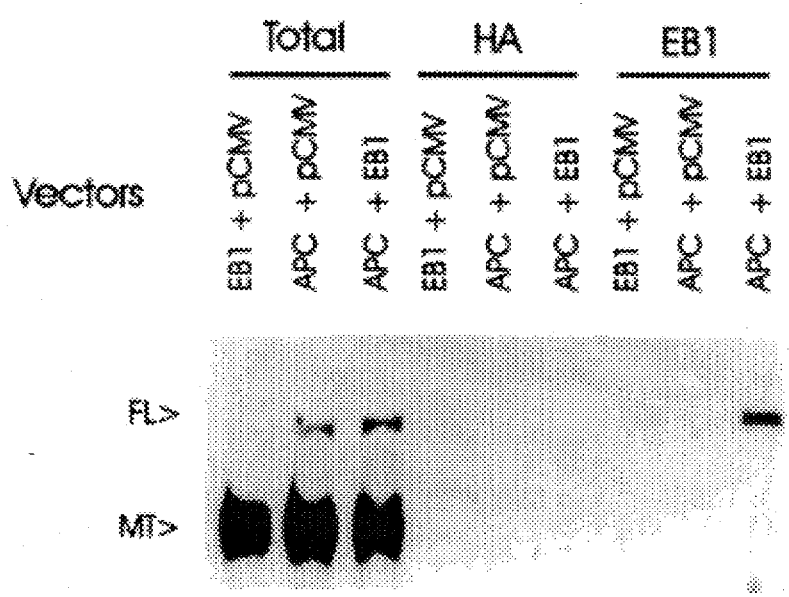
FIG. 3 shows in vivo association of APC and EB1. SW480 cells were transiently transfected with expression vectors for EB1 or APC as indicated. The parental expression vector pCMV-NEO-BAM (pCMV) was used to equalize the total amount of DNA transfected. Lysates prepared from these transfected cells were used directly (total), or after immunoprecipitation with a monoclonal antibody against hemagghtinin (HA) as negative control or an EB1-specific monoclonal antibody (EB1). Detection of APC was carried out by immunoblotting using APC specific monoclonal antibody FE9. MT and FL indicate truncated and full length APC, respectively.

In order to further characterize the association APC and EB1, three monoclonal antibodies (AE9, EA3 and GD10) against EB1 were generated. Western blot analysis with all three of these antibodies detected a 30 kD protein in total cell lysates which associated with GST-APCE, but not with a control protein GST-CTN. BB1 protein was detected in several human colon cancer cell lines including a human kidney fibroblast cell line 293, the canine kidney epithelial cell line MDCK, and the mouse fibroblast cell line NIH3T3. To demonstrate an in vivo association between EB1 and APC in mammalian cells, SW480 cells were transiently transfected with vectors expressing APC or BB1. The association between these two proteins was examined by immunoprecipitation using the EB1-specific antibody EA3 followed by immunoblotting with the APC-specific antibody FE9. The co-immunoprecipitation of APC and EB1 was clearly demonstrated when cells were transfected with both expression vectors but not when either one was omitted. (FIG. 3.)

We have not been able to detect the association between endogenous full-length APC and EB1 by co-immunoprecipitation experiments. The reason for this may be purely technical. This is consistent with our inability to co-immunoprecipitate APC and EB 1 from cell lysates prepared from yeast clones with clear functional evidence of an association between these two proteins as reflected by the two-hybrid assay. Similar reasons have also been suggested for the failure to demonstrate an association between pRB and RBP2 by co-immunoprecipitation (26, 27).

Methods: Monoclonal antibodies. The three EB1 monoclonal antibodies, AE9, EA3, and GD10, were derived from mice immunized with GST-EB1 fusion protein. Immunization of mice, cell fusion, and the preparation of monoclonal antibodies were carried out as described (27). The EA3 monoclonal was found to specifically recognize EB1 by both Western blot and immunoprecipitation. Methods: in vivo Binding Assay. SW480 cell lines were transiently transfected with pCMV-APC or pCMV-EB1. The pCMV-APC was as described (20) and the pCMVEB1 vector was derived by cloning a PCR product containing EB1 nucleotides 62 to 871 into the BamH1 site of pCMV-NEO-BAM. PCR was performed with following primers which were engineered to include the underlined BglII sites: 5-CGAGATCTAAGATGGCAGTGAACGTATAC-3' and 5'-GCAGATCTTTAATACTCTTCTTGATCCTCC-3'). To eliminate the possibility of PCR errors, the sequence of the EB1 fragment cloned into PCMV-EB1 was verified by nucleotide sequencing. Transient transfections, preparation of cell lysates, immunoprecipitation and western blot analysis were performed as described (16, 19, 20).

EXAMPLE 4

This example demonstrates the chromosomal mapping of EB1.

Figure 4:
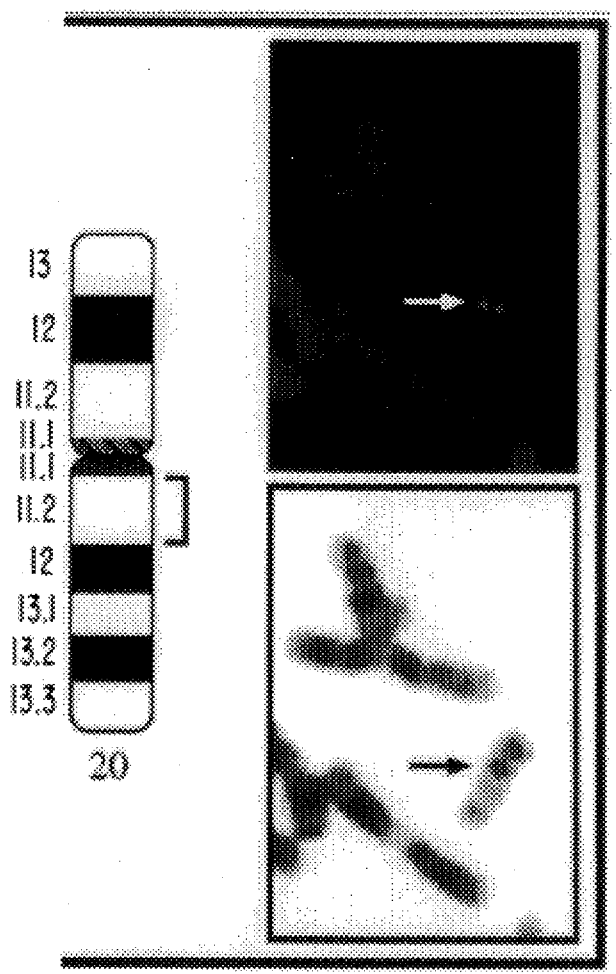
FIG. 4 shows the localization of EB1 to chromosome 20q11.2 by fluorescence in situ hybridization (FISH). The left panel shows an ideogram of a G-banded human chromosome 20 with the band q 11.2 bracketed. The top right panel shows the fluorescent signals localizing EB1 to chromosome 20. The bottom right panel shows a G-banded human chromosome 20 localizing EB1 to 20q11.2.

The chromosomal localization of EB1 was determined by fluorescence in situ hybridization (FISH). Three P1 clones for EB1 were isolated from a P1 library by PCR. One of these P1 clones was used as the probe in the FISH analysis as previously described (24). Sixteen out of a total of 17 metaphase cell examined displayed double fluorescent signals (i.e. one on each chromafin) on the proximal short arm of chromosome 20. The same cells hybridized for FISH had been previously G-banded and photographed to allow direct comparisons of the results. The result demonstrated that the sequences hybridizing to EB1 can be localized to 20q11.2 (FIG. 4).

Methods: Chromosomal localization. Three EB1 genomic clones 922, EB1–923, EB1–924) were obtained by PCR screening of A P1 library (Genome Systems, Inc.) using primers (5'-AAAACAGAGAGGCTGACCG-3 and 5'-ATTTCTCCACTGAGGTCGC-3') designed to amplify EB1 nucleotides 1102 to 1205. Total EB1-923 DNA was labeled with Biotin-16-dUTP by nick translation and used for FISH. For FISH, about 100 ng of probe was used in 10 μl hybridization mixture (55% formamide, 2X SSC, and 1 μg human Cot 1 DNA) which was denatured at 75° C. for 5 minutes. Hybridization was carried out using a modified procedure of Pinkel et at. (28) as previously described (29).

EXAMPLE 5

This example analyzes the nucleotide and amino acid sequences of EB1.

Searches of the National Center for Biotechnology Information (NCBI) non-redundant nucleotide and EST (expressed sequence tag) databases indicated that EB 1 had not been previously characterized although there were several ESTs that were almost identical to parts of the 3' untranslated region. Interestingly, there were also five ESTs which were similar but not identical to the coding region of EB1. These ESTs likely represented novel EB1-related genes rather than sequencing mistakes as there were numerous nucleotide substitutions that preserved the encoded amino acids of EBJ in these ESTs. These five ESTs could be divided into three contigs which represented at least two different EB1 related proteins (FIG. 5A). Searches of NCBI's non-redundant protein database with EB1 identified three proteins with statistically significant (P<0.05) multiple regions of homology. These were a calcium channel protein from carp (PIR #A37860,P =0075), a bacterial RNA polymerase sigma chain homolog (PXR#JN0445, P =0.0028) and Yer016p (P=$2.4 \times 10^{-53}$). Yer016p is a putafive gene identified in a 66,030 bp Saccharomyces cerevisiae chromosome V cosmid eontig (Genbank #U18778). The predicted Yer016p protein shared five blocks of similarity with EB1 and could represent a yeast homolog of EB1 (FIG. 5B). Together, these data suggest that EB1 is a member of a highly conserved multi-gene family.

Methods: Database searches and alignments. The NCBI's non redundant nucleotide, non-redundant protein and DBEST databases (1/19/95 releases) were searched using the BLASTN, BLASTP and TBLASTN basic local alignment search software, respectively (30). Multiple alignments were performed using the MACAW multiple alignment construction and analysis software version 2.03 (31).

References

1. Groden, J., Thliveris, A., Samowitz, W., Calson, M., Gelbert, L., Albertsen, H., Joslyn, G., Stevens, J., Spirio, L., Robertson, M., Sargeant, L., Krapcho, K., Wolff, E., Burt, R., Hughes, A. P., Warrington, I., McPherson, I., Wasmuth, 1., Le Paslier, D., Abderrahim, H., Cohen, D., Leppert, M., and White, R. Identification and characterization of the familial adenomatous polyposis coli gene. Cell, 66: 589–600, 1991.

3roslyn, G., Calson, M., Thliveris, A., Albertsen, H., Gelbert, L., Samowitz, W., Groden, J., Stevens, J., Spirio, L., Robertson, M., Sargeant, L., Krapcho, K., Wolff, E., Burt, R., Hughes, J. P., Warrington, J., McPherson, L, Wasmuth, Le Paslier, D., Abderrahim, H., Cohen, D., Leppert, M., and White, R. Identification of deletion mutations and three new genes at the Familial polyposis locus. Cell, 66: 601–613, 1991.

3. Kinzler, K. W., Nilbert, M. C., Su, L.-K., Vogelstein, B., Bryan, T. M., Levy, D. B., Smith, K. J., Preisinger, A. C., Hedge, P., McKeehnie, D., Finniear, R., Markham, A., Groffen, J., Boguski, M. S., Altsehul, S. F., Horii, A., Ando, H., Miyoshi, Y., Mild, Y., Nishisho, I., Nakamura, Y. Identification of FAP locus genes from chromosome 5q21. Science, 253: 661–665, 1991.

4. Nishisho, I., Nakamura, Y., Miyoshi, Y., Miki, Y., Ando, H., Horii, A., Koyama, K., Utsunomiya, J., Baba, S., Hedge, P., Markham, A., Kruch, A. J., Petersen, G., Hamilton, S. R., Nilbert, M. C., Levy, D. B., Bryan, T. M., Preisinger, A. C., Smith, K. J., Su, L.-K., Kinzler, K. W., Vogelstein, B. Mutations of chromosome 5q21 genes in FAP and colorectal cancer patients. Science, 253: 665–669, 1991.

5. Nagase, H., and Nakamura, Y. Mutations of the APC (adenomatous polyposis coli) gene. Human Mutation 2: 425–434, 1993.

6. Powell, S. M., Zilz, N., Beazer-Barclay, Y., Bryan, T. M., Hamilton, S. R., Thibodeau, S. N., Vogelstein, B., and Kinzler, K. W. APC mutations occur early during colorectal tumorigen.sis. Nature, 359: 235–237, 1992.

7. Miyoshi, Y., Nagas., H., Ando, H., Horii, A., Ichii, S., Nakatsuru, S., Aoki, T., Miki, Y., Mori, T., and Nakamura, Y. Somatic mutations of the APC gene in colorectal tumors: mutation cluster region in the APC gene. Human Molecular Genetics, 1: 229–233, 1992.

8. Miyaki, M., Konishi, M., Kikuchi-Yanoshita, R., Enomoto, M., Igar, T., Tanaka, K., Muraoka, M., Takahashi, H., Amada, Y., Fukayama, M., Maeda, Y., Iwama, T., Mishima, Y., Mori, T., and Koike, M. Characteristics of somatic mutation of the adenomatous polyposis coli gene in colorectal tumors. Cancer Research, 54: 3011–3020, 1994.

9. De Benedetti, L., Sciallero, S., Gismondi, V., James, R., Barico, A., Biticchi, R., Masettii, E., Bonelli, L., Heouaine, A., Picasso, M., Groden, J., Robertson, M., Risio, M., Caprilli, R., Bruzzi, P., White, R. L., Aste, H., Santi, L., Varesco, L., and Ferrara, G. B. Association of APC gene mutations and histological characteristics of colorectal adenomas. Cancer Research, 54: 3553–3556, 1994.

10. Jen, J., Powell, S. M., Papadopoulos, N., Smith, J., Hamilton, S. R., Vogelstein, B., and Kinzler, K. W. Molecular determinants of dysplasia in colorectal lesions. Cancer Research, 54: 5523–5526, 1994.

11. Smith, A. J., Stern, H. S., Penner, M., Hay, K., Mitri, A., Bapat, B. V., and Galling, S. Somatic APC and K-ras codon 2 mutations in aberrant crypt foci from human colons. Cancer Research, 54: 5527–5530, 1994.

12. Moser, A. R., Pitot, H. C., and Dove, W. F. A dominant mutation that predisposes to multiple intestinal neoplasia in the mouse. Science, 247: 322–324, 1990.

13. Su, L.-K., Kinzler, K. W., Volgelstein, B., Preisinger, A. C., Moser, A. R., Luongo, C., Gould, K. A., and Dove, W. F. Multiple intestinal neoplasia caused by a mutation in the murine homolog of the APC gene. Science, 256: 668–670, 1992.

14. Fodde, R., Edelmann, W., Yang, K., van Leeuwen, C., Carlson, C., Renault, B., Breukel, C., Alt, E., Lipkin, M., Meera Khan, P., and Kucherlapati, R. A targeted chain-termination mutation in the mouse Apc gene results in multiple intestinal tumors. Proc. Natl. Acad. Sci. USA, 91: 8969–8973, 1994.

15. Peifer, M., Berg, S., and Reynolds, A. B. A repeating amino acid motif shared by proteins with diverse cellular roles. Cell 76: 789–791, 1994.

16. Su, L.-K., Johnson, K. A., Smith K. J., Hill, D. E., Vogelstein, B., and Kinzler, K.W. Association between wild-type and mutant APC gene products. Cancer Research, 53: 2728–2731, 1993.

17. Joslyn, G., Richardson, D. S., White, R., and Alber, T. Dimer formation by an N-terminal coiled-coil in the APC protein. Proc. Natl. Acad. Sci. USA, 90: 11109–11113, 1993.

18. Rubinfeld, B., Souza, B., Albert, L, Muller, O., Chamberlain, S. H., Masiarz, F. R., Munemitsu, S., and Polakis, P. Association of the APC gene product with beta-catenin. Science, 262: 1731–1733, 1993.

19. Su, L.-K., Vogeistein, B., and Kinzler, K. W. Association of the APC tumor suppressor protein with catenins. Science, 262: 1734–1737, 1993.

20. Smith, K. J., Levy, D. B., Maupin, P., Pollard, T. D., Vogelstein, B., and Kinzler, K. W. Wild-type but not mutant APC associates with the microtubule cytoskeleton. Cancer Research, 54: 3672–3675, 1994.

21. Munemitsu, S., Souza, B., Muller, O., Albert, I., Rubinfeld, B., and Polakis, P. The APC gene product associates with microtubules in vivo and promotes their assembly in vitro. Cancer Research, 54: 3676–3681, 1994.

22. Fields, S., and Song, O.-K. A novel genetic system to detect protein protein interactions. Nature, 340: 245–246, 1989.

23. Gyuris, J., Golemis, E., Chertkov, H., and Brent, R. Cdi1, a human G1 and S phase protein phosphatase that associates with cdk2. Cell, 75: 791 803, 1993.

24. Ruden, D2 M., Ma, J., Li, Y., Wood, K., and Ptashne, M. Generating yeast transcriptional activators containing no yeast protein sequences. Nature, 350: 250–252, 1991.

25. Ron, D., and Dressler, H. pGSTag—A versatile bacterial expression plasmid for enzymatic labeling of recombinant proteins. BioTechniques, 13: 866–869, 1992.

26. Powell, S. M., Petersen, G. M., Krush, A. I., Booker, S., Jen, J., Giardiello, F. M., Hamilton, S. R., Vogelstein, B., and Kinzler, K. W. Molecular diagnosis 27. Smith, K. J., Johnson, K. A., Bryan, T. M., Hill, D. E., Markowitz, S., Wilson, J. K. V., Paraskeva, C., Petersen, G. M., Hamilton, S. R., Vogelstein, B., and Kinzler, K. W. The APC gene product in normal and tumor cells. *Proc. Natl. Acad. Sci. USA,* 90: 2846–2850, 1993.

28. Pinkel, D., Landegent, J., Collins, C., Fuscoe, J., Segraves, R., Lucas, J., and Gray, J. Fluorecence in situ hybridization with human chromosome-specific libraries: Detection of trisomy 21 and translocation of chromosome 4. *Proc. Natl. Acad. Sci. USA,* 85: 9138–9142, 1988.

29. Meltzer, P.S., Guan, X.-Y., Burgess, A., and Trent, J. M. Micro-FISH: a novel stategy to identify cryptic chromosomal rearrangements. *Nature Genet.,* 1: 24–28, 1992.

30. Altschul, S. F., Gish, W., Miller, W., Myers, E. W., and Lipman, D. J. Basic local alignment search tool. *J. Mol. Biol.* 215: 403–410, 1990.

31. Schuler, G. D., Altschul, S. F., and Lipman D. I. A workbench for multiple alignment construction and analysis. *Proteins Struct. Funct. Genet.* 9: 180–190, 1991.

32. Fattaey, A. R., Helin, K., Dembski, M. S., Dyson, N., Harlow, E., Vuosolo, G. A., Hanobik, M. G., Haskell, K. M., Oliff, A., Defe-Jones, D., and Jones, R. E. Characterization of the retinoblastoma binding proteins RBP1 and RBP2. *Oncogene,* 8: 3149–3156, 1993.

33. Kim, Y. W., Otterson, G. A., Kratzke, R. A., Coxon, A. B., and Kaye, F. J. Differential specificity for binding of retinoblastoma binding protein 2 to RB, p107, and TATA-binding protein. *Mol. Cell. Biol.,* 14: 7256 7264, 1994.

---

We claim:

1. An isolated and purified nucleic acid molecule comprising the EB1 set forth in SEQ ID NO:1.

2. The nucleic acid molecule of claim 1 further comprising a vector containing an origin of replication.

3. An isolated and purified nucleic add molecule comprising at least 18 contiguous nucleotides of the EB1 coding sequence, wherein said EB1 coding sequence consists of nucleotide residues 65 to 868 of SEQ ID NO: 1.

4. An isolated and purified nucleic acid molecule which comprises a coding sequence which encodes at least 20 contiguous amino acids of EB1 set forth in SEQ ID NO:2.

5. An isolated and purified nucleic acid molecule of at least 12 nucleotides, said nucleic acid molecule consisting of a contiguous sequence selected from residues 65 to 868 of SEQ ID NO:1.

6. An isolated and purified nucleic acid molecule that encodes a polypeptide of at least 6 amino acid residues, said polypeptide consisting of contiguous amino acid residues of SEQ ID NO:2.

* * * * *

UNITED STATES PATENT AND TRADEMARK OFFICE
CERTIFICATE OF CORRECTION

PATENT NO. : 5,736,389
DATED : April 7, 1998
INVENTOR(S) : Bert Vogelstein and Kenneth W. Kinzler It is certified that error appears in the above-identified patent and that said Letters Patent is hereby corrected as shown below:

Claim 1, line 2, after "EB1" insert --sequence--.

Signed and Sealed this

Eighteenth Day of August, 1998

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2540 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: EB1

( v i i i ) POSITION IN GENOME:
        ( A ) CHROMOSOME/SEGMENT: 20q11.2

( i x ) FEATURE:
        ( A ) NAME/KEY: CDS
        ( B ) LOCATION: 65..868

( x i ) SEQUENCE DESCRIPTION: SEQ ID NO:1:

```
ACGAGACGAA GACGGAACCG GAGCCGGTTG CGGGCAGTGG ACGCGGTTCT GCCGAGAGCC                    60

GAAG ATG GCA GTG AAC GTA TAC TCA ACG TCA GTG ACC AGT GAT AAC CTA                    109
     Met Ala Val Asn Val Tyr Ser Thr Ser Val Thr Ser Asp Asn Leu
     1               5                   10                  15

AGT CGA CAT GAC ATG CTG GCC TGG ATC AAT GAG TCT CTG CAG TTG AAT                     157
Ser Arg His Asp Met Leu Ala Trp Ile Asn Glu Ser Leu Gln Leu Asn
                20                  25                  30

CTG ACA AAG ATC GAA CAG TTG TGC TCA GGG GCT GCG TAT TGT CAG TTT                     205
Leu Thr Lys Ile Glu Gln Leu Cys Ser Gly Ala Ala Tyr Cys Gln Phe
            35                  40                  45

ATG GAC ATG CTG TTC CCT GGC TCC ATT GCC TTG AAG AAA GTG AAA TTC                     253
Met Asp Met Leu Phe Pro Gly Ser Ile Ala Leu Lys Lys Val Lys Phe
        50                  55                  60

CAA GCT AAG CTA GAA CAC GAG TAC ATC CAG AAC TTC AAA ATA CTA CAA                     301
```

```
        Gln Ala Lys Leu Glu His Glu Tyr Ile Gln Asn Phe Lys Ile Leu Gln
            65                  70                  75

GCA GGT TTT AAG AGA ATG GGT GTT GAC AAA ATA ATT CCT GTG GAC AAA     349
        Ala Gly Phe Lys Arg Met Gly Val Asp Lys Ile Ile Pro Val Asp Lys
        80                  85                  90                  95

TTA GTA AAA GGA AAG TTT CAG GAC AAT TTT GAA TTC GTT CAG TGG TTC     397
        Leu Val Lys Gly Lys Phe Gln Asp Asn Phe Glu Phe Val Gln Trp Phe
                            100                 105                 110

AAG AAG TTT TTC GAT GCA AAC TAT GAT GGA AAA GAC TAT GAC CCT GTG     445
        Lys Lys Phe Phe Asp Ala Asn Tyr Asp Gly Lys Asp Tyr Asp Pro Val
                    115                 120                 125

GCT GCC AGA CAA GGT CAA GAA ACT GCA GTG GCT CCT TCC CTT GTT GCT     493
        Ala Ala Arg Gln Gly Gln Glu Thr Ala Val Ala Pro Ser Leu Val Ala
                130                 135                 140

CCA GCT CTG AAT AAA CCG AAG AAA CCT CTC ACT TCT AGC AGT GCA GCT     541
        Pro Ala Leu Asn Lys Pro Lys Lys Pro Leu Thr Ser Ser Ser Ala Ala
        145                 150                 155

CCC CAG AGG CCC ATC TCA ACA CAG AGA ACC GCT GCG GCT CCT AAG GCT     589
        Pro Gln Arg Pro Ile Ser Thr Gln Arg Thr Ala Ala Ala Pro Lys Ala
        160                 165                 170                 175

GGC CCT GGT GTG GTG CGA AAG AAC CCT GGT GTG GGC AAC GGA GAC GAC     637
        Gly Pro Gly Val Val Arg Lys Asn Pro Gly Val Gly Asn Gly Asp Asp
                            180                 185                 190

GAG GCA GCT GAG TTG ATG CAG CAG GTC AAC GTA TTG AAA CTT ACT GTT     685
        Glu Ala Ala Glu Leu Met Gln Gln Val Asn Val Leu Lys Leu Thr Val
                    195                 200                 205

GAA GAC TTG GAG AAA GAG AGG GAT TTC TAC TTC GGA AAG CTA CGG AAC     733
        Glu Asp Leu Glu Lys Glu Arg Asp Phe Tyr Phe Gly Lys Leu Arg Asn
                210                 215                 220

ATT GAA TTG ATT TGC CAG GAG AAC GAG GGG GAA AAC GAC CCT GTA TTG     781
        Ile Glu Leu Ile Cys Gln Glu Asn Glu Gly Glu Asn Asp Pro Val Leu
        225                 230                 235

CAG AGG ATT GTA GAC ATT CTG TAT GCC ACA GAT GAA GGC TTT GTG ATA     829
        Gln Arg Ile Val Asp Ile Leu Tyr Ala Thr Asp Glu Gly Phe Val Ile
        240                 245                 250                 255

CCT GAT GAA GGG GGC CCA CAG GAG GAG CAA GAA GAG TAT TAACAGCCTG      878
        Pro Asp Glu Gly Gly Pro Gln Glu Glu Gln Glu Glu Tyr
                            260                 265

GACCAGCAGA GCAACATCGG AATTCTTCAC TCCAAATCAT GTGCTTAACT GTAAATACT          938

CCCTTTTGTT ATCCTTAGAG GACTCACTGG TTTCTTTTCA TAAGCAAAAA GTACCTCTTC         998

TTAAAGTGCA CTTTGCAGAC GTTCACTCC TTTTCCAATA AGTTTGAGTT AGGAGCTTTT         1058

ACCTTGTAGC AGAGCAGTAT TAACATCTAG TTGGTTCACC TGGAAAACAG AGAGGCTGAC        1118

CGTGGGGCTC ACCATGCGGA TGCGGGTCAC ACTGAATGCT GGAGAGATGT ATGTAATATG        1178

CTGAGGTGGC GACCTCAGTG GAGAAATGTA AAGACTGAAT TGAATTTTAA GCTAATGTGA        1238

AATCAGAGAA TGTTGTAATA AGTAAATGCC TTAAGAGTAT TTAAAATATG CTTCCACATT        1298

TCAAAATATA AAATGTAACA TGACAAGAGA TTTTGCGTTT GACATTGTGT CTGGGAAGGA        1358

AGGGCCAGAC CTTGGAACCT TTGGAACCTG CTGTCAACAG GTCTTACAGG GCTGCTTGAA        1418

CCCTCATAGG CCTAGGCTTT GGTCTAAAAG GAACATTTAA AAAGTTGCCC TGTAAAGTTA        1478

TTTGGTGTCA TTGACCAATT GCATCCCAGC TAAAAAGCAA GAGGCATCGT TGCCTGGATA        1538

ATAGAGGATG TGTTTCAGCC CTGAGATGTT ACAGTTGAAG AGCTTGGTTT CATTGAGCAT        1598

TTCTCTATTT TTCCAGTTAT CCCGAAATTT CTATGTATTA TTTTTGGGG AAGTGAGGTG        1658

TGCCCAGTTT TTTAATCTAA CAACTACTTT TGGGGACTTG CCCACATCTC TGGGATTTGA        1718

ATGGGGATTG TATCCCATTT TACTGTCTTT TAGGTTTACA TTTACCACGT TTCTCTTCTC        1778
```

```
TGCTCCCCTT GCCCACTGGG ACTCCTCTTT GGCTCCTTGA AGTTTGCTGC TTAGAGTTGG    1838
AAGTGCAGCA GGCAGGTGAT CATGCTGCAA GTTCTTTCTG GACCTCTGGC AAAGGGAGTG    1898
GTCAGTGAAG GCCATCGTTA CCTTGGGATC TGCCAGGCTG GGTGTTTTC GGTATCTGCT     1958
GTTCACAGCT CTCCACTGTA ATCCGAATAC TTTGCCAGTG CACTAATCTC TTTGGAGATA    2018
AAATTCATTA GTGTGTTACT AAATGTTAAT TTTCTTTTGC GGAAAATACA GTACCGTGTC    2078
TGAATTAATT ATTAATATTT AAAATACTTC ATTCCTTAAC TCTCCCTCAT TTGCTTTGCC    2138
CACAGCCTAT TCAGTTCCTT TGTTTGGCAG GATTCTGCAA AATGTGTCTC ACCCACTACT    2198
GAGATTGTTC AGCCCCTGAT GTATTTGTAT TGATTTGTTT CTGGTGGTAG CTTGTCCTGA    2258
AATGTGTGTA GAAAGCAAGT ATTTTATGAT AAAAATGTTG TGTAGTGCAT GCTCTGTGTG    2318
GAATTCAGAG GAAAACCCAG ATTCAGTGAT TAACAATGCC AAAAAATGCA AGTAACTAGC    2378
CATTGTTCAA ATGACAGTGG TGCTATTTCT CTTTGTGGC CTTTAGACT TTGTTGCCC       2438
TAAAATTCCA TTTTATTGGG AACCCATTTT CCACCTGGTC TTTCTTGACA GGGTTTTTT     2498
CTACTTTAAA CAGTTCTAA ATAAAATTCT GTATTCAAA AA                         2540
```

( 2 ) INFORMATION FOR SEQ ID NO:2:

( i ) SEQUENCE CHARACTERISTICS:
        ( A ) LENGTH: 268 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Val Asn Val Tyr Ser Thr Ser Val Thr Ser Asp Asn Leu Ser
 1               5                  10                  15

Arg His Asp Met Leu Ala Trp Ile Asn Glu Ser Leu Gln Leu Asn Leu
                20                  25                  30

Thr Lys Ile Glu Gln Leu Cys Ser Gly Ala Ala Tyr Cys Gln Phe Met
            35                  40                  45

Asp Met Leu Phe Pro Gly Ser Ile Ala Leu Lys Lys Val Lys Phe Gln
        50                  55                  60

Ala Lys Leu Glu His Glu Tyr Ile Gln Asn Phe Lys Ile Leu Gln Ala
65                  70                  75                  80

Gly Phe Lys Arg Met Gly Val Asp Lys Ile Ile Pro Val Asp Lys Leu
                85                  90                  95

Val Lys Gly Lys Phe Gln Asp Asn Phe Glu Phe Val Gln Trp Phe Lys
            100                 105                 110

Lys Phe Phe Asp Ala Asn Tyr Asp Gly Lys Asp Tyr Asp Pro Val Ala
        115                 120                 125

Ala Arg Gln Gly Gln Glu Thr Ala Val Ala Pro Ser Leu Val Ala Pro
    130                 135                 140

Ala Leu Asn Lys Pro Lys Lys Pro Leu Thr Ser Ser Ser Ala Ala Pro
145                 150                 155                 160

Gln Arg Pro Ile Ser Thr Gln Arg Thr Ala Ala Pro Lys Ala Gly
                165                 170                 175

Pro Gly Val Val Arg Lys Asn Pro Gly Val Gly Asn Gly Asp Asp Glu
            180                 185                 190

Ala Ala Glu Leu Met Gln Gln Val Asn Val Leu Lys Leu Thr Val Glu
        195                 200                 205

Asp Leu Glu Lys Glu Arg Asp Phe Tyr Phe Gly Lys Leu Arg Asn Ile
    210                 215                 220
```

```
Glu Leu Ile Cys Gln Glu Asn Glu Gly Glu Asn Asp Pro Val Leu Gln
225                 230                 235                 240

Arg Ile Val Asp Ile Leu Tyr Ala Thr Asp Glu Gly Phe Val Ile Pro
                245                 250                 255

Asp Glu Gly Gly Pro Gln Glu Glu Gln Glu Glu Tyr
            260                 265
```

(2) INFORMATION FOR SEQ ID NO:3:

(i) SEQUENCE CHARACTERISTICS:
        (A) LENGTH: 149 amino acids
        (B) TYPE: amino acid
        (D) TOPOLOGY: linear (ii) MOLECULE TYPE: peptide (iii) HYPOTHETICAL: YES (iv) ANTI-SENSE: NO (vi) ORIGINAL SOURCE:
        (A) ORGANISM: Homo sapiens (vii) IMMEDIATE SOURCE:
        (B) CLONE: EB2

(xi) SEQUENCE DESCRIPTION: SEQ ID NO:3:

```
Ile Ala Trp Val Asn Asp Ile Val Ser Leu Asn Tyr Thr Lys Val Glu
1               5                   10                  15

Gln Leu Cys Ser Gly Ala Ala Tyr Cys Gln Phe Met Asp Met Leu Phe
                20                  25                  30

Pro Gly Cys Ile Ser Leu Lys Lys Val Lys Phe Gln Ala Lys Leu Glu
            35                  40                  45

His Glu Tyr Ile His Asn Phe Lys Leu Leu Gln Ala Ser Phe Lys Arg
        50                  55                  60

Met Asn Val Asp Lys Val Ile Pro Val Glu Lys Leu Val Lys Gly Arg
65                  70                  75                  80

Phe Gln Asp Asn Leu Asp Phe Ile Gln Trp Phe Lys Lys Phe Tyr Asp
                85                  90                  95

Ala Asn Tyr Asp Gly Lys Glu Tyr Asp Pro Val Glu Ala Arg Gln Gly
            100                 105                 110

Gln Asp Ala Ile Pro Pro Pro Asp Pro Gly Glu Gln Ile Phe Asn Leu
        115                 120                 125

Pro Lys Lys Ser His His Ala Asn Ser Pro Thr Ala Gly Ala Ala Lys
    130                 135                 140

Phe Lys Phe Gln Xaa
145
```

(2) INFORMATION FOR SEQ ID NO:4:

(i) SEQUENCE CHARACTERISTICS:
        (A) LENGTH: 344 amino acids
        (B) TYPE: amino acid
        (D) TOPOLOGY: linear (ii) MOLECULE TYPE: peptide (iii) HYPOTHETICAL: YES (iv) ANTI-SENSE: NO (vi) ORIGINAL SOURCE:
        (A) ORGANISM: Saccharomyces cerevisiae (vii) IMMEDIATE SOURCE:

(B) CLONE: Yer016p (xi) SEQUENCE DESCRIPTION: SEQ ID NO:4:

| Met | Ser | Ala | Gly | Ile | Gly | Glu | Ser | Arg | Thr | Glu | Leu | Leu | Thr | Trp | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asn | Gly | Leu | Leu | Asn | Leu | Asn | Tyr | Lys | Lys | Ile | Glu | Glu | Cys | Gly | Thr |
|     |     |     | 20  |     |     |     |     | 25  |     |     |     |     | 30  |     |     |
| Gly | Ala | Ala | Tyr | Cys | Gln | Ile | Met | Asp | Ser | Ile | Tyr | Gly | Asp | Leu | Pro |
|     |     | 35  |     |     |     |     | 40  |     |     |     |     | 45  |     |     |     |
| Met | Asn | Arg | Val | Lys | Phe | Asn | Ala | Thr | Ala | Glu | Tyr | Glu | Phe | Gln | Thr |
|     | 50  |     |     |     |     | 55  |     |     |     |     | 60  |     |     |     |     |
| Asn | Tyr | Lys | Ile | Leu | Gln | Ser | Cys | Phe | Ser | Arg | His | Gly | Ile | Glu | Lys |
| 65  |     |     |     |     | 70  |     |     |     |     | 75  |     |     |     |     | 80  |
| Thr | Val | Tyr | Val | Asp | Lys | Leu | Ile | Arg | Cys | Lys | Phe | Gln | Asp | Asn | Leu |
|     |     |     |     | 85  |     |     |     |     | 90  |     |     |     |     | 95  |     |
| Glu | Phe | Leu | Gln | Trp | Leu | Lys | Lys | His | Trp | Ile | Arg | His | Lys | Asp | Glu |
|     |     |     | 100 |     |     |     |     | 105 |     |     |     |     | 110 |     |     |
| Ser | Val | Tyr | Asp | Pro | Asp | Ala | Arg | Arg | Lys | Tyr | Arg | Pro | Ile | Ile | Thr |
|     |     | 115 |     |     |     |     | 120 |     |     |     |     | 125 |     |     |     |
| Asn | Asn | Ser | Ala | Thr | Lys | Pro | Arg | Thr | Val | Ser | Asn | Pro | Thr | Thr | Ala |
|     | 130 |     |     |     |     | 135 |     |     |     |     | 140 |     |     |     |     |
| Lys | Arg | Ser | Ser | Ser | Thr | Gly | Thr | Gly | Ser | Ala | Met | Ser | Gly | Gly | Leu |
| 145 |     |     |     |     | 150 |     |     |     |     | 155 |     |     |     |     | 160 |
| Ala | Thr | Arg | His | Ser | Ser | Leu | Gly | Ile | Asn | Gly | Ser | Arg | Lys | Thr | Ser |
|     |     |     |     | 165 |     |     |     |     | 170 |     |     |     |     | 175 |     |
| Val | Thr | Gln | Gly | Gln | Leu | Val | Ala | Ile | Gln | Ala | Glu | Leu | Thr | Lys | Ser |
|     |     |     | 180 |     |     |     |     | 185 |     |     |     |     | 190 |     |     |
| Gln | Glu | Thr | Ile | Gly | Ser | Leu | Asn | Glu | Glu | Ile | Glu | Gln | Tyr | Lys | Gly |
|     |     | 195 |     |     |     |     | 200 |     |     |     |     | 205 |     |     |     |
| Thr | Val | Ser | Thr | Leu | Glu | Ile | Glu | Arg | Glu | Phe | Tyr | Phe | Asn | Lys | Leu |
|     | 210 |     |     |     |     | 215 |     |     |     |     | 220 |     |     |     |     |
| Arg | Asp | Ile | Glu | Ile | Leu | Val | His | Thr | Thr | Gln | Asp | Leu | Ile | Asn | Glu |
| 225 |     |     |     |     | 230 |     |     |     |     | 235 |     |     |     |     | 240 |
| Gly | Val | Tyr | Lys | Phe | Asn | Asp | Glu | Thr | Ile | Thr | Gly | His | Gly | Asn | Gly |
|     |     |     |     | 245 |     |     |     |     | 250 |     |     |     |     | 255 |     |
| Asn | Gly | Gly | Ala | Leu | Leu | Arg | Phe | Val | Lys | Lys | Val | Glu | Ser | Ile | Leu |
|     |     |     | 260 |     |     |     |     | 265 |     |     |     |     | 270 |     |     |
| Tyr | Ala | Thr | Ala | Glu | Gly | Phe | Glu | Met | Asn | Asp | Gly | Glu | Asp | Glu | Leu |
|     |     | 275 |     |     |     |     | 280 |     |     |     |     | 285 |     |     |     |
| Asn | Asp | Lys | Asn | Leu | Gly | Glu | His | Gly | Thr | Val | Pro | Asn | Gln | Gly | Gly |
|     | 290 |     |     |     |     | 295 |     |     |     |     | 300 |     |     |     |     |
| Tyr | Ala | Asn | Ser | Asn | Gly | Glu | Val | Asn | Gly | Asn | Glu | Gly | Ser | Asn | His |
| 305 |     |     |     |     | 310 |     |     |     |     | 315 |     |     |     |     | 320 |
| Asp | Val | Ile | Met | Gln | Asn | Asp | Glu | Gly | Glu | Val | Gly | Val | Ser | Asn | Asn |
|     |     |     |     | 325 |     |     |     |     | 330 |     |     |     |     | 335 |     |
| Leu | Ile | Ile | Asp | Glu | Glu | Thr | Phe |     |     |     |     |     |     |     |     |
|     |     |     | 340 |     |     |     |     |     |     |     |     |     |     |     |     |

(2) INFORMATION FOR SEQ ID NO:5:

(i) SEQUENCE CHARACTERISTICS:
 (A) LENGTH: 112 amino acids
 (B) TYPE: amino acid
 (D) TOPOLOGY: linear (ii) MOLECULE TYPE: peptide ( i i i ) HYPOTHETICAL: YES ( i v ) ANTI-SENSE: NO ( v i ) ORIGINAL SOURCE:
    ( A ) ORGANISM: Homo sapiens ( v i i ) IMMEDIATE SOURCE:
    ( B ) CLONE: z19434

( x i ) SEQUENCE DESCRIPTION: SEQ ID NO:5:

```
Asp Glu Asp Pro Pro Pro Arg Ser Arg Arg Pro Glu Pro Gln Pro Leu
1               5                   10                  15

Pro Gln Arg Pro Arg His Leu Ser Pro Pro Pro Pro Pro Pro Pro Glu
                20                  25                  30

Pro Pro Arg Ala Leu Trp Gly Met Ala Val Asn Val Tyr Ser Thr Ser
            35                  40                  45

Val Thr Ser Glu Asn Leu Ser Arg His Asp Met Leu Ala Trp Val Asn
        50                  55                  60

Asp Ser Leu His Leu Asn Tyr Thr Lys Ile Glu Gln Leu Cys Ser Gly
65                  70                  75                  80

Ala Ala Tyr Cys Gln Phe Met Asp Met Leu Phe Pro Gly Cys Val His
                85                  90                  95

Leu Arg Lys Val Lys Phe Gln Gly Lys Leu Gly His Xaa Tyr Ile His
                100                 105                 110
```

( 2 ) INFORMATION FOR SEQ ID NO:6:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: peptide ( i i i ) HYPOTHETICAL: YES ( i v ) ANTI-SENSE: NO ( v i ) ORIGINAL SOURCE:
    ( A ) ORGANISM: Homo sapiens ( v i i ) IMMEDIATE SOURCE:
    ( B ) CLONE: M85402

( x i ) SEQUENCE DESCRIPTION: SEQ ID NO:6:

```
Asn Phe Lys Val Leu Gln Xaa Ala Phe Lys Met Gly Val Asp Lys
1               5                   10                  15

Ile Ile Pro Val Glu Lys Leu Val Lys Gly Lys Phe Gln Asp Asn Phe
                20                  25                  30

Xaa Phe Ile Gln Trp Phe Lys Lys Xaa Phe Asp Ala Asn Tyr Asp Gly
            35                  40                  45

Lys Asp Tyr Asn Pro Leu Leu Ala Arg Gln Gly Gln Asp Val Ala Pro
        50                  55                  60

Pro Pro Asn Pro Val Pro Gln Arg Thr Ser Pro Thr Gly Pro Lys Asn
65                  70                  75                  80

Met Gln Thr Ser Gly Arg Leu Ser Asn Val Ala Pro Pro Cys Ile Leu
                85                  90                  95

Arg Lys Xaa Pro Pro Ser Ala Arg Asn Gly Gly His Glu Thr Cys Pro
                100                 105                 110

Asn Ser Leu Asn Ser Asn Gln Gln
                115                 120
```

( 2 ) INFORMATION FOR SEQ ID NO:7:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GGATCCTAAT ACGACTCACT ATAGGGAGAC CACCATGGCA GTGAACGTAT ACTC    54

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

ATTTCTCCAC TGAGGTCGC    19

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

CGAGATCTAA GATGGCAGTG AACGTATA    28

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

GCAGATCTTT AATACTCTTC TTGATCCTCC    30

( 2 ) INFORMATION FOR SEQ ID NO:11:

( i ) SEQUENCE CHARACTERISTICS:
        ( A ) LENGTH: 19 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

AAAACAGAGA GGCTGACCG                                                                                19

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

ATTTCTCCAC TGAGGTCGC                                                                                19